United States Patent [19]
Krebs

[11] Patent Number: 5,496,281
[45] Date of Patent: Mar. 5, 1996

[54] SPINAL CANNULA WITH TRANSPARENT GRIP PART

[76] Inventor: Peter Krebs, Waldstrasse 39, 78048 VS-Villingen, Germany

[21] Appl. No.: 312,109

[22] Filed: Sep. 26, 1994

[30] Foreign Application Priority Data

Mar. 26, 1994 [DE] Germany .......................... 69405166 U

[51] Int. Cl.$^6$ .................................................. A61M 5/178
[52] U.S. Cl. ...................... 604/168; 604/900; 604/272
[58] Field of Search ........................... 604/264, 27, 48, 604/51, 53, 158, 161, 162, 164, 165, 166, 168, 170, 171, 272, 280, 283, 900; 128/763, 754, 753

[56] References Cited

U.S. PATENT DOCUMENTS

| | | |
|---|---|---|
| D. 302,589 | 8/1989 | McMenamy . |
| D. 303,290 | 9/1989 | McMenamy . |
| D. 342,995 | 1/1994 | Simmons . |
| D. 353,454 | 12/1994 | Coombs . |
| 4,137,916 | 2/1979 | Killman et al. ............ 604/170 X |
| 4,308,875 | 1/1982 | Young ..................... 604/164 X |
| 4,356,828 | 11/1982 | Jamshidi . |
| 4,585,444 | 4/1986 | Harris ...................... 604/177 |
| 4,609,370 | 9/1986 | Morrison . |
| 4,721,506 | 1/1988 | Teves . |
| 4,828,549 | 5/1989 | Kvalo ...................... 604/164 |
| 4,846,799 | 7/1989 | Tanaka et al. ............ 604/164 X |
| 4,981,892 | 1/1991 | Nishida et al. .......... 524/291 |
| 4,994,036 | 2/1991 | Biscoping et al. ........ 604/51 X |
| 5,030,205 | 7/1991 | Holdaway et al. ........ 604/164 |
| 5,100,390 | 3/1992 | Lubeck et al. ............ 604/158 |
| 5,104,381 | 4/1992 | Gresl et al. ............... 604/51 X |
| 5,106,376 | 4/1992 | Mononen et al. ........ 604/48 X |
| 5,116,323 | 5/1992 | Kreuzer . |
| 5,161,542 | 11/1992 | Palestrant . |
| 5,250,035 | 10/1993 | Smith et al. ............... 604/168 X |
| 5,306,259 | 4/1994 | Fischell . |

FOREIGN PATENT DOCUMENTS

| | | |
|---|---|---|
| 2328261 | 12/1973 | Germany . |
| 3421170 | 4/1986 | Germany . |
| 3900329 | 7/1990 | Germany . |
| 4038952 | 6/1992 | Germany . |

*Primary Examiner*—Corrine M. Maglione
*Assistant Examiner*—N. Kent Gring
*Attorney, Agent, or Firm*—McGlew and Tuttle

[57] ABSTRACT

The spinal cannula 1 is provided with a grip part, which consists of transparent plastic and surrounds the rear end of the cannula in a substance-securing manner. A cerebrospinal fluid checking chamber, which tapers toward the rear end of the cannula and is visible from the outside, is located in it, and this cerebrospinal fluid checking chamber is joined on the rear side by a conical plug-type Luer bore for accommodating the Luer plug-type cone of a drug syringe in a positive-locking manner. On the outside, the grip part has, between two flange parts, at least two, radially recessed grip surfaces, which are arranged diametrically opposed to one another and symmetrically to a plane of symmetry located in the longitudinal axis, and between which the cerebrospinal fluid checking chamber is arranged. In addition, there is a stylet, which can be introduced into the cannula through the cerebrospinal fluid checking chamber. The cerebrospinal fluid checking chamber extends at least approximately over the axial distance a between the two flange parts, and it has an essentially rectangular cross-sectional shape with flat wall surfaces extending in pairs in a wedge-shaped pattern in relation to one another, wherein one pair of wall surfaces is arranged symmetrically to the plane of symmetry of the grip surfaces, and has a wedge angle that is substantially smaller than the wedge angle of the other pair of wall surfaces.

16 Claims, 2 Drawing Sheets

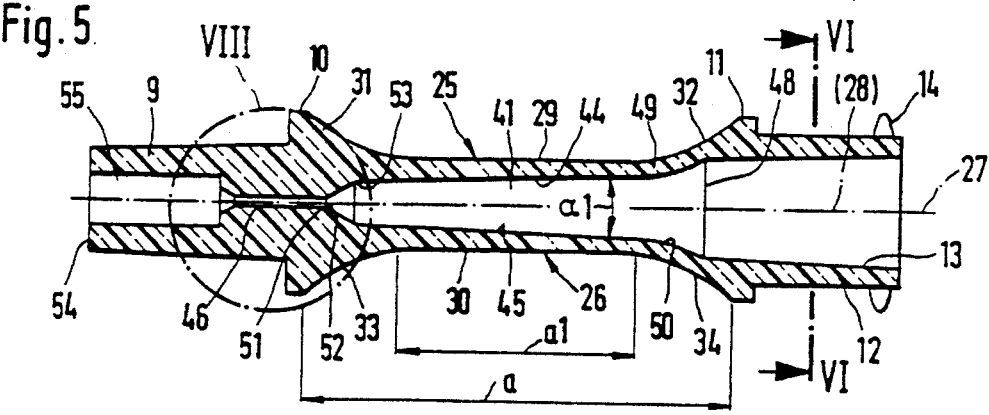
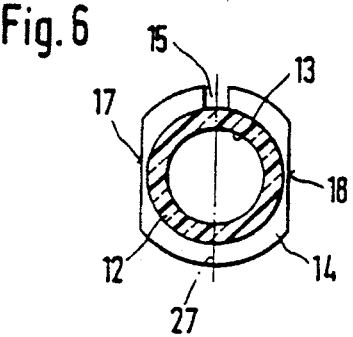
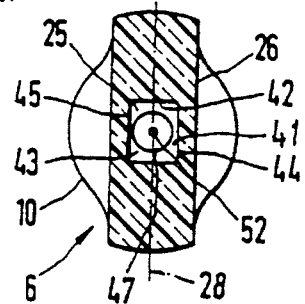
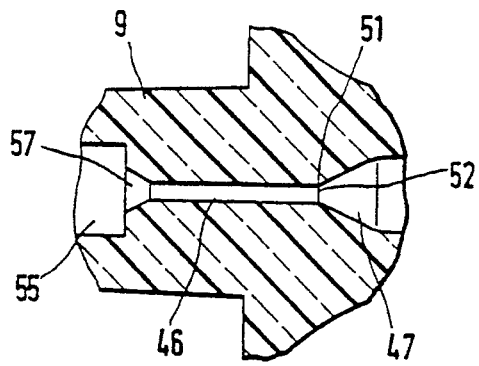
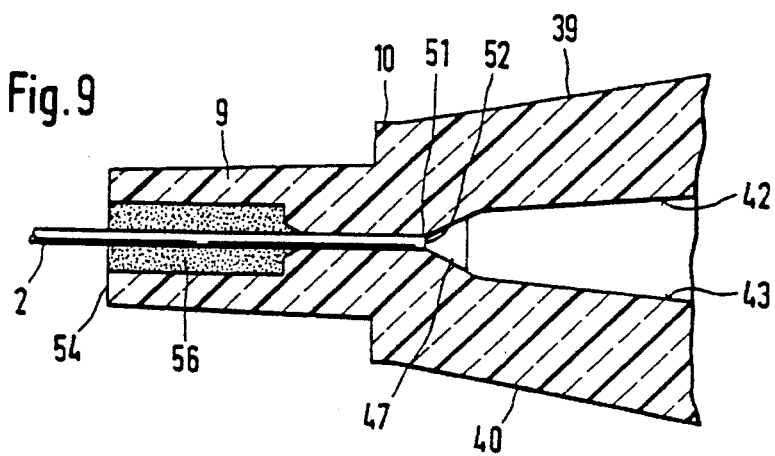

5,496,281

SPINAL CANNULA WITH TRANSPARENT GRIP PART

FIELD OF THE INVENTION

The present invention pertains to a spinal cannula with a grip part which consists of a transparent plastic, surrounds the rear end of the cannula in a substance-securing manner, and in which a cerebrospinal fluid checking chamber, which is visible from the outside and tapers toward the rear end of the cannula, is located, wherein the cerebrospinal fluid checking chamber is joined on the rear side by a conical, plug-type Luer bore for accommodating the Luer plug-type cone of a drug syringe in a positive-locking manner, and wherein the grip part has, on the outside, between two flange parts, at least two radially recessed grip surfaces, which oppose each other diametrically and are symmetrical to a plane of symmetry located in the longitudinal axis, and between which the cerebrospinal fluid checking chamber is arranged, as well as with a stylet, which can be introduced into the cannula through the cerebrospinal fluid checking chamber.

BACKGROUND OF THE INVENTION

Such spinal cannulas are used to puncture the vertebral canal. To make it possible to check the correct positioning of the tip of the cannula in the subarachnoidal space, it is important to optically clearly recognize and check the reflux of the cerebrospinal fluid into the cerebrospinal fluid checking chamber. In addition, secure holding of the cannula and good guiding must be guaranteed.

Numerous spinal cannulas of this class, which have a transparent grip part at the rear end of the cannula, have already been known. In some embodiments of these prior-art spinal cannulas, the cerebrospinal fluid checking chamber of the grip part is conical over its entire length, whereas in other embodiments it is conical only over approximately half the axial length, the rest being of cylindrical design. Some grip parts are provided with two diametrically opposed, recess-like grip surfaces arched uniformly over the entire length, while others have flat or stepped grip surfaces. In addition, a spinal cannula has been known, whose grip part has a plurality of radial ribs, which surround a cerebrospinal fluid checking chamber, which is conical as a whole, at regular axial distances.

Optical effects, such as reflections, refractions, and similar phenomena, which interfere with the visual checking of the reflux of cerebrospinal fluid within the cerebrospinal fluid checking chamber, occur in all prior-art spinal cannulas.

In addition, the cerebrospinal fluid checking chamber in most prior-art spinal cannulas is too short to make it possible to check the flow of cerebrospinal fluid over a sufficiently long section and time.

SUMMARY AND OBJECTS OF THE INVENTION

The primary object of the present invention is to design the grip part of a spinal cannula such that interfering optical effects in the area of the cerebrospinal fluid checking chamber will be avoided, on the one hand, as a result of which the reflux of cerebrospinal fluid occurring during dural puncture can be optically readily recognized and checked over a sufficiently long section and time, and that the cannula can be accurately and easily guided with the grip part, on the other hand.

This object is attained according to the present invention by the cerebrospinal fluid checking chamber, which extends at least approximately over the axial distance between the two flange parts, having an essentially rectangular cross-sectional shape with wall surfaces extending in pairs in the manner of wedges in relation to one another, wherein one pair of wall surfaces is arranged symmetrically to the plane of symmetry of the grip surfaces and has a wedge angle that is substantially smaller than the wedge angle of the other pair of wall surfaces.

The cross-sectional shape of the cerebrospinal fluid checking chamber, is designed according to the present invention, and the at least approximately parallel arrangement of the grip surfaces in relation to one of the pairs of wall surfaces ensure that the reflux of cerebrospinal fluid within the cerebrospinal fluid checking chamber can be very easily recognized without interfering reflections and refractions of light, especially when the observer looks at one of the grip surfaces at approximately fight angles. In addition, there is only a relatively slight, but uniformly linear increase in the cross section of the cerebrospinal fluid checking chamber in the direction of flow of the cerebrospinal fluid, which also makes it possible for the observer to monitor or recognize the uniformity of the flow of the cerebrospinal fluid, which also provides him with information on the correct position of the tip of the cannula in the subarachnoidal space.

The two grip surfaces designed according to the present invention also make possible the good and accurate guiding as well as easy and secure holding of the grip part during both puncture and the injection of an anesthetic by means of an attached syringe.

The grip surfaces are preferably flat middle sections each of which extend in parallel to one anther and are joined by concave curves which lead to the peripheral edges of the flange parts. The grip surfaces are broader in the area of their flat middle sections than the two flange parts and the greatest width of the grip parts is located approximately in their axial center. The grip surfaces have an overall elliptical surface shape with respect to a top view. The section of the grip part located between the two flange parts has a contour which is partly arc-shaped and partly wedge-shaped, in a top view of one of the respective grip surfaces. The cannula is inserted into a central axial bore. The central axial bore opens directly into a rear-side, conical plug-type Luer bore in the area of a rear flange part. At this region two wall surfaces with the greater wedge angle extend as straight surfaces from the conical section to the common edge with the conical plug-type Luer bore. Two wall surfaces with a smaller wedge angle join the plug-type Luer bore with a short, spherical curve. The axial bore accommodating the rear the section of the cannula ends at a radial stop shoulder. Short curved transitions are located between the straight wall surfaces and the conical section.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 5 is a section V—V from FIG. 4;

FIG. 6 is a section VI—VI from FIG. 5;

FIG. 7 is a section VII—VII from FIG. 4;

FIG. 8 is an enlarged detail VIII from FIG. 5; and

FIG. 9 is a somewhat enlarged representation of the left-hand part of FIG. 4 with the cannula inserted.

DETAILED DESCRIPTION OF THE PREFERRED EMBODIMENTS

Figure 1:
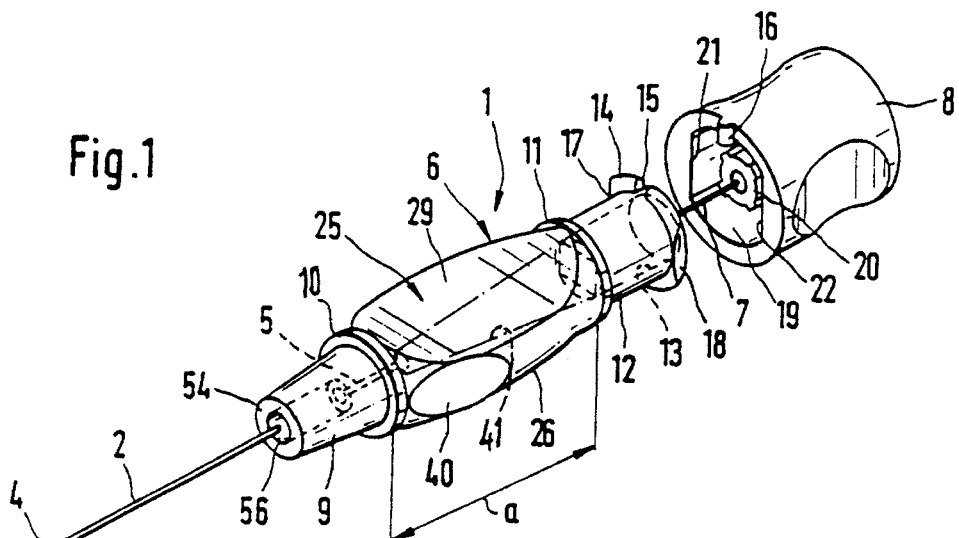
FIG. 1 is a perspective view of a spinal cannula with a stylet.

The spinal cannula 1 shown in the drawing has a thin cannula (hollow needle) 2 with a piercing tip 3, which is provided with an opening 4, and whose rear end section 5 is fastened in a one-piece grip part 6 consisting of transparent plastic.

In addition, the spinal cannula 1 is provided with a stylet 7, which has a handle 8, designed as a cap-like hollow body, at its distal end. The stylet 7 can be introduced into the cannula 2 through the hollow grip part 6, to the extent that the opening 4 at the piercing tip can be closed by the front end of the stylet 7.

The grip part 6 is manufactured as a one-piece injection molding; it consists of methyl methacrylate-butadiene-styrene (MBS), which is characterized not only by glass-like optical properties, especially a glass-clear transparency, but also by a high, accurately controllable flowability during the injection molding process, so that very high precision can be guaranteed during the manufacture.

On the proximal end facing the piercing tip 3 of the hollow needle, the grip part 6 is provided with a so-called Luer plug-type cone, which is joined by a first, cylindrical flange part 10 of a larger diameter. At an axial distance of ca. 17 to 18 mm, there is a second flange part 11 of equal size, which is joined by a cylindrical shoulder 12, at a distal end of the grip part 6 in which a plug-type Luer bore 13, which is used for the positive-locking accommodation of the Luer plug-type cone of a drug syringe, not shown, is located. However, it is also possible, for special applications, to introduce a second, smaller cannula, which is equipped with the same grip part 6, and whose plug-type cone 9 fits the plug-type Luer bore 13, into the spinal cannula 1 instead of the stylet 7.

A flange ring 14, which is provided with flattened areas 17 and 18 on both sides, and has a recess 15 on the top side shown in FIG. 1, is arranged at the distal end of the cylindrical end section 12. The flange ring 14 is used to adjust the angle of the handle 8, which has, in an axial recess 19, a centering pin 20 fitting the plug-type Luer bore 13 and a guide rib 16, which is introduced into the recess 15 of the flange ring 14 when the handle 8 is pushed over the end section 12 up to the flange part 11. As can be recognized from FIG. 1, the recess 19 of the handle 8 is also provided with two lateral flattened areas 21 and 22, respectively, which are adapted to the flattened areas 17 and 18 of the flange ring 14.

The angular adjustment of the handle 8 and consequently of the stylet 7 as well is necessary because the stylet 7 is usually provided, at its proximal end, with a polished section, which is adapted to the piercing tip 3 and to the opening 4, and it must assume an accurately specified fitting position during the introduction of the piercing tip into the vertebral canal through the epidural space.

Two grip surfaces 25 and 26, which are radially recessed in relation to the flange parts 10 and 11, and which are arranged diametrically opposed to one another and are symmetrical to a plane of symmetry 28 located in the central axis 27 of the grip part 1, are located between the two flange parts 10 and 11. Each of the grip surfaces 25, 26 has a flat middle section 29 and 30, respectively, which extends in parallel to the plane of symmetry 28, and which are bilaterally joined by respective concave curves 31, 32 and 33, 34, which lead to the peripheral edges 35, 36 of the flange parts 10 and 11, respectively. Thus, the grip surfaces 25, 26 have, on the whole, an elliptical surface shape in the top view. The flat middle sections 29 and 30 extending in parallel to one another extend over an axial length, which is located in the middle between the two flange parts 10 and 11. The length al corresponds to approximately two thirds of a.

Figure 2:
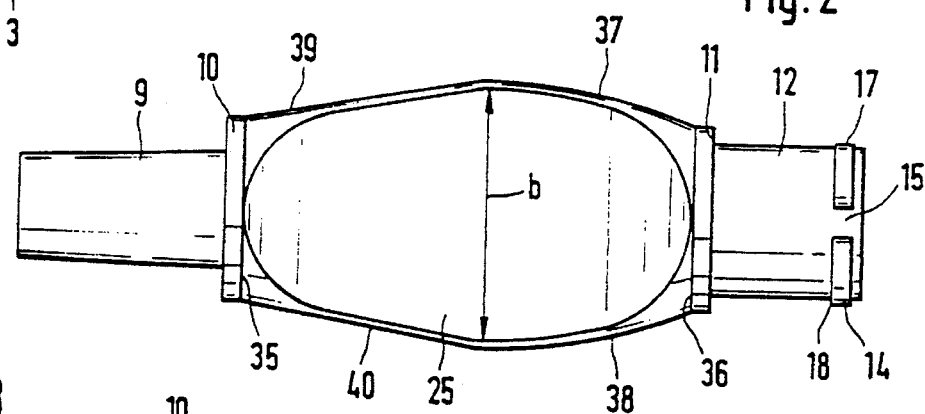
FIG. 2 is a top view of the grip part of the spinal cannula.
Figure 3:
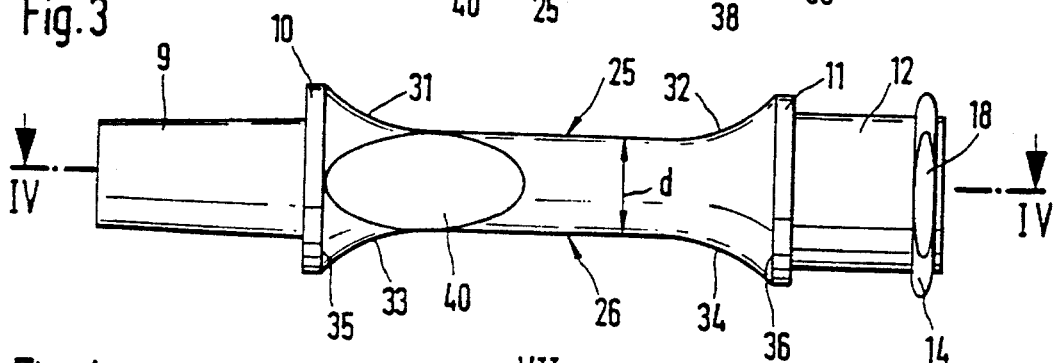
FIG. 3 is a side view of the grip part of the spinal cannula.
Figure 4:
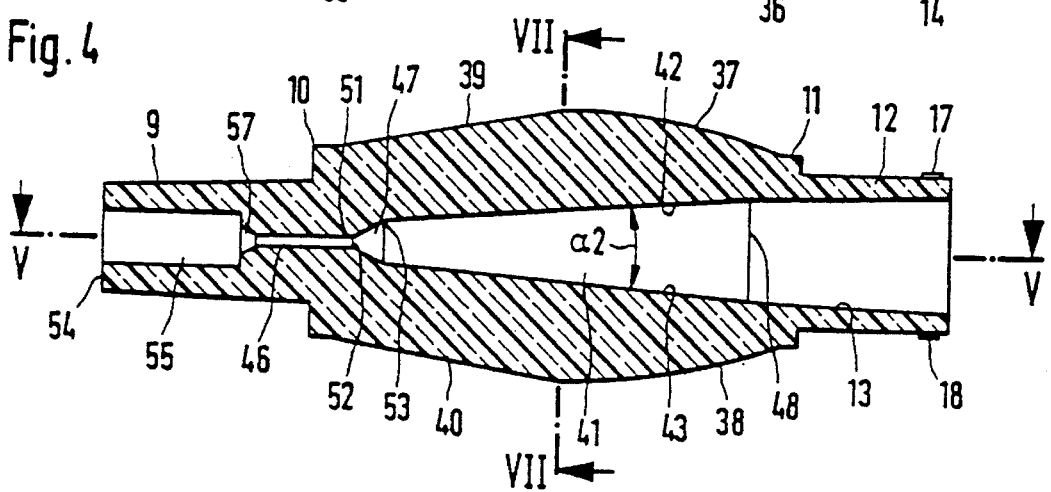
FIG. 4 is a section IV—IV from FIG. 3.

As is apparent from FIGS. 1, 2 and 4, the grip surfaces 25, 26 are broader in the area of their respective middle sections 29 and 30 than the two flange parts 10 and 11, and the section of the grip part 6 located between the two flange parts 10, 11 has a contour which forms a respective arc 37 and 38, respectively, in the top view of one of the grip surfaces 25, 26 in the distal half, and a flattened wedge surface 39 and 40, respectively, in the proximal half, and this contour is also symmetrical to the central axis 27 (FIGS. 5 and 6).

A cerebrospinal fluid checking chamber 41, which extends at least approximately over the entire distance a and has an essentially rectangular cross-section shape with flat wall surfaces 42, 43 and 44, 45, which extend in pairs in a wedge-shaped pattern in relation to one another, is located inside the grip part 6 between the two flange parts 10 and 11. The pair 44/45 of wall surfaces is arranged symmetrically to the plane of symmetry 28, to which the two grip surfaces 25 and 26 are also arranged symmetrically. While the two wall surfaces 44 and 45 have a wedge angle $\alpha 1$ of ca. 4°, the other two wall surfaces 42 and 43, which are extended at right angles to them, have a wedge angle $\alpha 2$ that is more than twice the above-mentioned angle, namely, ca. 10°.

The three-dimensional shape of the cerebrospinal fluid checking chamber 41 thus corresponds at least approximately to the three-dimensional shape of a straight pyramid with a rectangular base with its tip cut off.

As is apparent from FIG. 7, the wall surfaces 44 and 45, which are on the whole broader, are, on the whole, parallel to one of the two grip surfaces 25 and 26, respectively, aside from the wedge angle $\alpha 1$, while the narrower wall surfaces 42 and 43 extend at right angles to these grip surfaces.

As a result, interfering optical phenomena, such as reflections and refractions of light, are avoided when the cerebrospinal fluid checking chamber 41 is viewed through one of the two grip surfaces 25, 26.

The cerebrospinal fluid checking chamber 41, which is wedge-shaped over its entire axial length, begins in the vicinity of the front, cannula-side proximal end flange part 10 at a central axial bore 46, which fittingly accommodates the distal end section 5 of the cannula 2, with a short, conical section 47, and it opens in the area of the distal end flange part 11 directly into the distal end, conical plug-type Luer bore 13. The two wall surfaces 42, 43 with the greater wedge angle $\alpha 2$ extend from the conical section 47 to the common edge 48, while the other two wall surfaces 44, 45 with the small wedge angle $\alpha 1$ join the plug-type bore 13 with a short, spherical curve 49 and 50, respectively.

To obtain an axial stop for the distal end of the cannula during the introduction of the cannula 2 into the axial bore 46, which is adapted to its diameter, the axial bore 46 is provided with a radial stop shoulder 51, which is formed by the conical section 47 ending in a central opening 52, whose diameter is smaller than the diameter of the axial bore 46, and which is at most of the same size as, but preferably smaller than the internal diameter of the cannula 2. It is ensured as a result that the stylet 7 to be introduced into the cannula 2 from the rear side through the cerebrospinal fluid checking chamber 41 will reliably reach the tubular hollow space of the cannula, without the stylet's 7 tip being caught at any edge.

In a preferred embodiment, the axial bore 46 and the cannula 2 have a diameter of 0.42 mm, and the opening 52 has a diameter of 0.25 mm, while the internal diameter of the cannula is ca. 0.3 mm.

The axial length of the conical section 47 is preferably ca. 1 mm to 2 mm, and a rounded transition 53 is advantageously provided between the flat wall surfaces 42 and 43 as well as 44 and 45, on the one hand, and the said conical section 47, on the other hand. An expanded, cylindrical adhesive chamber 55, which is open on the front side and is filled with a suitable, preferably two-component adhesive 56 for fastening the cannula 2 in the grip part 6, is provided between the axial bore 47 fittingly accommodating the distal end section 5 of the cannula 2 and the front end face 54 of the Luer plug-type cone 9.

To facilitate the introduction of the rear end section 5 of the cannula 2 into the axial bore 46, the proximal end of the axial bore 46 is provided with a conical expansion 57.

In a preferred exemplary embodiment, the distance a and consequently the overall length of the two grip surfaces 25 and 26 is ca. 16.5 mm at a width b of ca. 9.5 mm. The thickness d in the area of the middle sections 29 and 30 of the grip surfaces 25 and 26 is ca. 3.5 mm in this preferred exemplary embodiment.

While a specific embodiment of the invention has been shown and described in detail to illustrate the application of the principles of the invention, it will be understood that the invention may be embodied otherwise without departing from such principles.

What is claimed:

1. A spinal cannula and grip part, comprising:

a grip part formed of a transparent plastic with a cerebrospinal fluid checking chamber defined within the grip part, said cerebrospinal fluid checking chamber being visible through said transparent plastic of said grip part, said grip part having a proximal end and a distal end, said distal end having a conical Luer plug-type bore, said grip part having an outer surface with a first flange located adjacent to said Luer bore and a second flange and grip surfaces disposed diametrically opposed and symmetrically with respect to a plane of symmetry located in a longitudinal axis of the grip part, said grip surface being recessed radially with respect to said first flange part and said second flange part, said cerebrospinal fluid checking chamber being arranged between said grip surfaces with said cerebrospinal fluid checking chamber extending substantially over an axial distance between said first flange part and said second flange part, said cerebrospinal fluid checking chamber having a taper toward a proximal end of said grip part, said cerebrospinal fluid checking chamber having a substantially rectangular cross-sectional shape defined by a first pair of opposed flat wall surfaces and a second pair of opposed flat wall surfaces, said first pair of wall surfaces being provided in a wedge shape and said second pair of wall surfaces being provided in a wedge shape, said first pair of wall surfaces being arranged symmetrically with respect to said plane of symmetry of said grip surfaces and having an angle defining said wedge shape which is smaller than an angle defining said wedge shape of said second pair of wall surfaces;

a cannula extending into a proximal end of said grip part;

a Luer plug-type cone disposed in a positive locking manner in said Luer plug-type bore; and a stylet positioned in said cannula extending through said cerebral fluid checking chamber.

2. Spinal cannula and grip part, comprising:

a cannula;

a grip part formed of a transparent plastic, said grip part surrounding a distal end section of said cannula said grip part defining within the grip part a cerebrospinal fluid checking chamber which tapers towards said distal end section of the cannula, said grip part having a proximal end and a distal end said checking chamber being visible from outside of said grip part, said cerebrospinal fluid checking chamber being joined on said distal end of said grip part by a conical Luer plug-type bore, said grip part having an outer surface with two flange parts and radially recessed grip surfaces, between said two flange parts, said radially recessed grip surfaces being arranged diametrically opposed to each other and symmetrically to a plane of symmetry located in a longitudinal axis of said grip part, said cerebrospinal fluid checking chamber being arranged between said grip surfaces, said cerebrospinal fluid checking chamber extending at least approximately over an axial distance between said two flange parts, said cerebrospinal fluid checking chamber having an essentially rectangular cross-sectional shape with flat wall surfaces, said flat wall surfaces extending in pairs in a wedge-shaped pattern relative to one another, a first pair of said flat wall surfaces being arranged symmetrically to the said plane of symmetry at said grip surfaces and having a wedge angle that is substantially smaller than a wedge angle of a second pair of said wall surfaces;

a Luer plug-type cone of a drug syringe positioned in a positive-locking manner in said Luer plug-type bore;

and a stylet positioned to be introduced into said cannula through said cerebrospinal fluid checking chamber.

3. Spinal cannula according to claim 2, wherein said radially recessed grip surfaces each have flat middle sections which extend in parallel to one another and are joined by concave curves leading to peripheral edges of said flange parts.

4. Spinal cannula according to claim 3, wherein said radially recessed grip surfaces are broader in an area of said middle sections than said flange parts, said grip parts having a greatest width located approximately at an axial center.

5. Spinal cannula according to claim 3, wherein said radially recessed grip surfaces have an overall elliptical surface shape with respect to a top view.

6. Spinal cannula according to claim 2, wherein a section of said grip part located between said two flange parts has a contour which partly arc-shaped and partly wedge-shaped in a top view of one of said respective grip surfaces.

7. Spinal cannula according to claim 2, wherein said cerebrospinal fluid checking chamber beings adjacent to said proximal end of said grip part on a proximal end side of said two flange parts and includes a conical section with a length substantially between 1mm to 2mm and includes a central axial bore, a distal end section of said cannula being inserted into said central axial bore and opening into a distal end of said conical Luer plug-type bore said second pair of wall surfaces extending as straight surfaces from said conical section to a common edge with said conical Luer plug-type bore, said first pair of wall surfaces joining said Luer plug-type bore with a short, spherical curve.

8. Spinal cannula according to claim 7, wherein said axial bore ends at a radial stop shoulder.

9. Spinal cannula according to claim 7, further comprising a central opening between said conical section and said central axial bore, said central opening having a diameter which is smaller than a diameter or said central axial bore, said central opening having a diameter which is no larger than an internal diameter of said cannula.

10. Spinal cannula according to claim 7, wherein a short curved transition section is located between said straight wall surfaces and said conical section.

11. Spinal cannula according to claim 2, wherein said smaller wedge angle of said wall surfaces is between 2° and 5° and said greater wedge angle of said wall surfaces is between 8° and 12°.

12. Spinal cannula according to claim 11, wherein said smaller wedge angle is 4° and said greater wedge angle is 10°.

13. Spinal cannula according to claim 2, wherein said grip surfaces have an axial length substantially equal to 16.5 mm and a maximum width of 9.5 mm, a thickness of said grip in an area of said middle sections of said grip surfaces being substantially 3.5 mm.

14. Spinal cannula according to claim 2, further comprising a Luer plug-type cone at a proximate end of said grip part.

15. Spinal cannula according to claim 2, wherein said grip part is formed in one piece of methyl methacrylate polymer.

16. Spinal cannula according to claim 14, wherein said methyl methacrylate polymer is methyl methacrylate-butadiene-styrene (MBS).

* * * * *